United States Patent [19]
Imran

[11] Patent Number: 5,357,979
[45] Date of Patent: Oct. 25, 1994

[54] FLEXIBLE ELONGATE DEVICE HAVING A DISTAL EXTREMITY WITH CURRENT CONTROLLED ADJUSTABLE STIFFNESS AND ADJUSTABLE BEND LOCATION AND METHOD

[75] Inventor: Mir A. Imran, Palo Alto, Calif.

[73] Assignee: Intelliwire, Inc., Sunnyvale, Calif.

[21] Appl. No.: 116,666

[22] Filed: Sep. 3, 1993

Related U.S. Application Data

[63] Continuation-in-part of Ser. No. 983,899, Dec. 1, 1992, abandoned.

[51] Int. Cl.$^5$ .............................................. A61B 5/00
[52] U.S. Cl. .................................... 128/772; 604/282
[58] Field of Search ................ 604/95, 264, 281, 282; 128/45 M, 772

[56] References Cited

U.S. PATENT DOCUMENTS

| | | | |
|---|---|---|---|
| 5,078,684 | 1/1992 | Yasuda | 604/281 |
| 5,114,402 | 5/1992 | McCoy | 604/95 |
| 5,188,111 | 2/1993 | Yates et al. | 604/95 |

FOREIGN PATENT DOCUMENTS

WO91/11213 8/1991 PCT Int'l Appl.

Primary Examiner—Jerome L. Kruter
Attorney, Agent, or Firm—Flehr, Hohbach, Test, Albritton & Herbert

[57] ABSTRACT

Flexible elongate device comprising a flexible elongate member having proximal and distal extremities, a shape-memory element is disposed in the flexible elongate member and is capable of assuming martensitic and austenitic states and has first and second portions. A layer of conductive material is formed on at least one of said portions. The layer has a conductivity greater than that of the shape-memory element. Electrical current is supplied to the shape-memory element. The conductive layer serves to conduct current and shunts current flow around that portion of the shape-memory element having the layer of conductive material thereon.

21 Claims, 2 Drawing Sheets

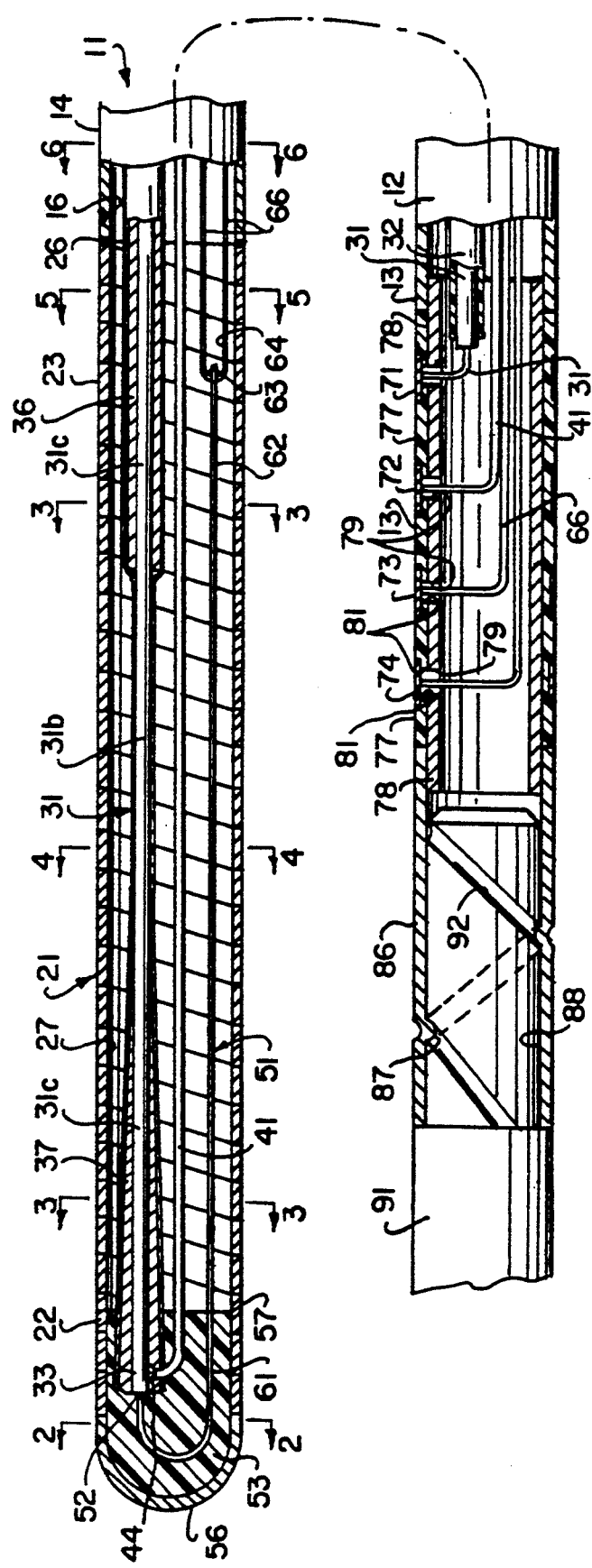

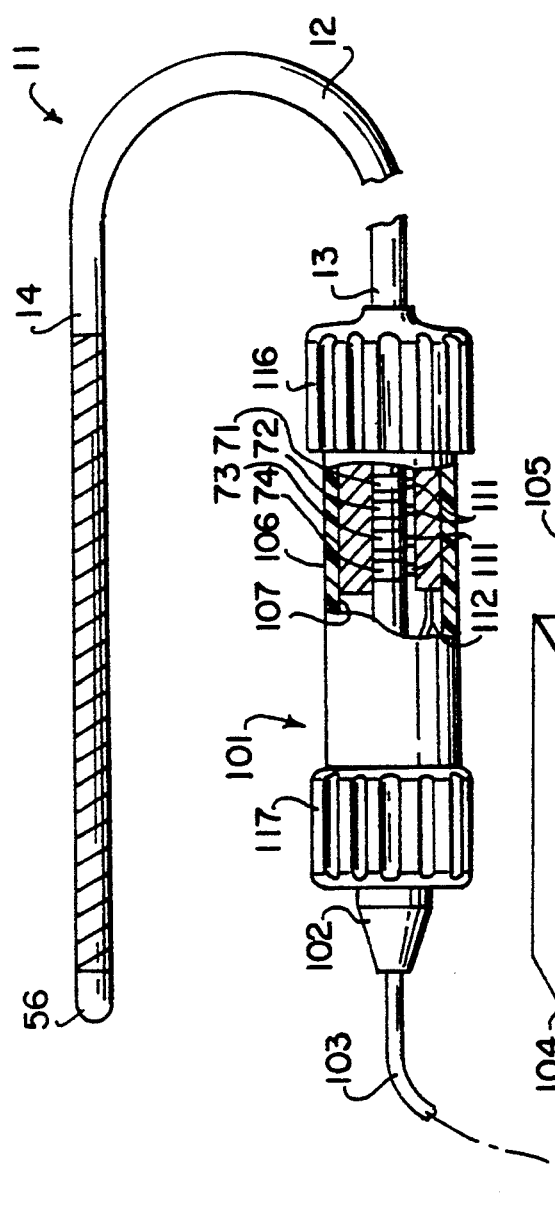
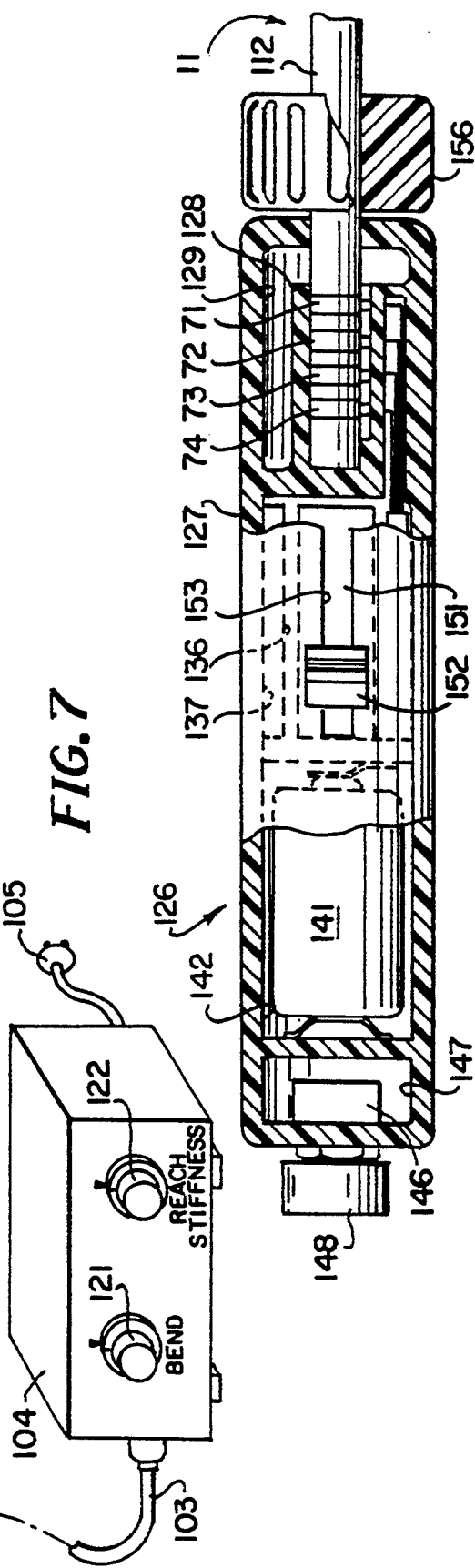

FLEXIBLE ELONGATE DEVICE HAVING A DISTAL EXTREMITY WITH CURRENT CONTROLLED ADJUSTABLE STIFFNESS AND ADJUSTABLE BEND LOCATION AND METHOD

This application is a continuation-in-part of application Ser. No. 07/983,899 filed on Dec. 1, 1992 now abandoned.

This invention relates to a flexible elongate device having a distal extremity with current controlled adjustable stiffness and adjustable bend location and method which is particularly adapted for use as a guide wire or a catheter.

In co-pending application Ser. No. 07/983,899 filed on Dec. 1, 1992 there is disclosed a flexible elongate device having a distal extremity of adjustable stiffness and method. It has been found that with such a device and method when utilized in connection with a steering mechanism having shape-memory elements that are heated to achieve steering, there has been a tendency for the heat generated by such steering elements to migrate to shape-memory elements which are utilized to achieve adjustable stiffness to cause them to stiffen in an undesirable manner and at a time when such stiffening is not desired. In addition it has been found that with such devices it is desirable to provide an adjustable bend location which is not possible with the device and method disclosed in said co-pending application Ser. No. 07/983,899 filed Dec. 1, 1992. There is therefore need for a new and improved flexible elongate device which overcomes these disadvantages.

In general, it is an object of the present invention to provide a flexible elongate device which has a distal extremity with current controlled adjustable stiffness and current controlled adjustable bend location and method.

Another object of the invention is to provide a flexible elongate device of the above character in which steering capabilities are provided.

Another object of the invention is to provide a device and method of the above character in which steering is accomplished in a single plane.

Another object of the invention is to provide a device and method of the above character in which the steering elements for steering are thermally isolated from elements for adjusting the stiffness and adjusting the bend location.

Another object of the invention is to provide a device and method of the above character in which the stiffness and bend location can be adjusted independent of each other.

Another object of the invention is to provide a device and method of the above character in which smooth transitions can be made in stiffness as well as in locations of the bend.

Another object of the invention is to provide a device and method of the above character in which fewer joints are required making the electrical connections for the elements utilized for steering, adjusting the stiffness and adjusting the bend location.

Another object of the present invention is to provide a device and method of the above character which can be rotated and which also can be docked with other devices.

Additional objects and features of the invention will appear from the following description in which the preferred embodiments are set forth in detail in conjunction with the accompanying drawings.

FIG. 1 is a side elevational view partially in cross section of a flexible elongate device having distal extremity with current controlled adjustable stiffness and adjustable bend location incorporating the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a cross-sectional view taken along the line 5—5 of FIG. 1.

FIG. 6 is a cross-sectional view taken along the line 6—6 of FIG. 1.

FIG. 7 is a plan view of the device shown in FIG. 1 connected to a handle which is connected to a control console.

FIG. 8 is an alternative embodiment of a handle for use in the device shown in FIG. 7.

In general, the flexible elongate device of the present invention is comprised of a flexible elongate member having proximal and distal extremities. A shape-memory element is disposed in the distal extremity. The shape-memory element has at least first and second portions. A conductive plating is formed on the first portion and has a thickness which tapers longitudinally of the shape-memory element. Means is provided for supplying electrical current to the shape-memory element for changing the stiffness of the shape-memory element and for adjusting the bend location of the shape-memory element.

More particularly, as shown in the drawings, the flexible elongate device 11 having a distal extremity with current controlled adjustable stiffness and adjustable bend location consists of a flexible elongate tubular member 12 which is provided with proximal and distal extremities 13 and 14. It can be formed of a suitable material such as stainless steel typically called a hypo tube having a suitable outside diameter, as for example 0.010 inches with a wall thickness of 0.0015 inches to provide a bore 16 of 0.007 inches in diameter extending from the proximal extremity 13 to the distal extremity 14.

A helical coil spring 21 is provided which has proximal and distal extremities 22 and 23. It can be formed of a suitable material such as platinum or a platinum tungsten alloy to provide the desired radiopacity. The wire forming the coil spring 21 can have a suitable size, as for example a diameter of 0.003 inches with the outside diameter of the spring 21 not exceeding the 0.010 inch diameter of the hypo tube 12. The proximal extremity 22 of the coil spring 21 is secured to the distal extremity 14 of the flexible elongate tubular member 12 by suitable means such as a weld 26. The coil spring 21 is provided with an interior passage 27.

A shape-memory element 31 formed of a suitable material such as Nitinol extends from the proximal extremity 13 of the hypo tube 12 through the bore 16 and into the passage 27 of the coil spring 21. The shape-memory element 31 is provided with at least three portions 31a, 31b and 31c which are spaced-apart longitudinally of the shape-memory element from the proximal extremity 32 to the distal extremity 33.

A conductive plating 36 is provided on the portion 31a of the shape-memory element. A conductive plating 37 is provided on the portion 31c with no conductive plating being provided on the portion 31b to achieve the adjustable stiffness and the adjustable bend location for the flexible elongate device 11.

As can be seen, the conductive plating 37 provided on the distal portion 31c of the shape-memory element 31 is provided with a gradient or in other words is tapered so that the plating is the thickest at the distal extremity and gradually tapers down to a zero thickness. The conductive plating 37 can extend for a suitable distance, as for example 1–2 centimeters from the distal extremity of the shape-memory element 31. By way of example, the plating 37 can have a maximum thickness of 40–50 micro-inches tapering down to 0 micro inches.

There is no plating on the intermediate portion of 31b which can extend a suitable distance, as for example from 1–2 centimeters. The conductive plating 36 begins at a distance of 3–5 centimeters from the distal extremity 33 and can have a suitable substantially uniform thickness, as for example 30–40 microinches throughout the remainder of the shape-memory element 31 extending to its proximal extremity 32.

The conductive material which is utilized for the conductive plating 36 and 37 has a conductivity greater than that of the shape-memory element 31 and can be a suitable material such as silver which can be deposited by electroplating in a manner well known to those skilled in the art to provide a plating of uniform thickness or to provide a plating such as plating 37 having a tapered or gradient thickness. The higher conductive plating 36 and 37 serves to shunt current flow around the shape-memory element. As hereinafter described, the plating 36 is provided to eliminate the need for making joints between the shape-memory element 31 and a conductor, as for example a silver-coated copper conductor which can be used for carrying the current to the shape-memory element during operation of the same as hereinafter described.

A return conductor 41 is provided which can be of a suitable type such as an insulated copper conductor 42 having a silver coating 43 to increase its conductivity. The conductor 41 can have a suitable diameter, as for example 0.001 inches. This conductor 41 is secured to the distal extremity of the conductive plating 37 and the distal extremity of the shape-memory element portion 31c by suitable means such as spot welding at 44 (see FIG. 1). An insulating coating 46 is provided on the outer surface of the silver coating 43 and is formed of a suitable insulating material such as a polyimide or a Nylon. An insulating coating 47 is also provided on the exterior of the shape-memory element 31 and extends over the conductive plating 36 and 37 so that the shape-memory element 31 as well as the conductor 41 are insulated from the coil spring 21 as well as from the flexible elongate tubular member 12 in the form of a hypo tube.

A pull element 51 formed of a suitable material such as a polyester fiber or a Kevlar fiber is bonded to the distal extremity of the shape-memory element 31 by a suitable means such as an adhesive 52 (see FIG. 1). As shown in FIG. 1, the pull element 51 extends distally and then loops proximally through 180° through the passage 27 of the coil spring 21. As shown in FIG. 1, the distal extremity of the shape-memory element 31, the distal extremity of the conductor 41 where it is connected to the shape-memory element 31 as well as the distal extremity of the pull element 51 are all embedded in a conventional ceramic epoxy that is relatively hard and stiff and acts as an insulator. This ceramic epoxy 53 fills a hollow generally hemispherical tip 56 formed of a suitable radiopaque material such as platinum and which is bonded to the distal extremity 23 of the coil spring 21 by suitable means such as a weld 57.

Only a single pull element 51 has been provided since in connection with the present invention it is desired to bend the distal extremity of the coil spring 21 only in a single plane. However, it should be appreciated that if desired, multi-plane bending can be achieved merely by adding at least two additional pull elements (not shown) connected in the same manner to the distal extremity of the shape-memory element 31 but spaced circumferentially about the shape-memory element 31 to achieve bending in the desired directions.

As can be seen, the pull element 51 is provided with a distal extremity 61 which is secured to the distal extremity of the shape-memory element 31 and is embedded in the epoxy 53. It also has a proximal extremity 62 disposed in the passage 27 of the coil spring 21. The distal extremity 62 is secured by suitable means such as a knot 63 to a pull wire 66 which has been formed into a loop 64 to double back on itself (see FIG. 1) and extends proximally through the bore 16 of the flexible elongate tubular member 12. This pull wire 66 is formed of a suitable material having a negative coefficient of expansion such as Nitinol so that it contracts upon being heated. This pull wire 66 is also provided with an insulating coating 67 formed of a suitable insulating material such as polyimide so that it is insulated from the flexible elongate tubular member 12.

With the arrangement shown, it can be seen that the pull wire 66 is positioned so that it is staggered or offset with respect to the distal extremity of the shape-memory element 31. This heat generated by the pull wire 66 is thermally isolated from the conductive plating 37 and also from the portions 31b and 31c of the shape-memory element 31 so that such heat cannot adversely effect the performance of the conductive plating 37 for providing an adjustable bend location as hereinafter described and also for providing a shape-memory element 31 having an adjustable stiffness as hereinafter described.

Means is provided for making electrical contact to the shape-memory element 31, the return conductor 51 as well as to the pull wire 66 and consists of annular slip rings 71, 72, 73 and 74 which can be a part of a flex circuit 76 in the form of a plastic sleeve 77 and which has one end bonded to the distal extremity 14 by a suitable means such as an epoxy (not shown). The flexible plastic sleeve 77 is supported by an inner sleeve 78 formed of a suitable material such as stainless steel which has one end mounted by a slip fit within the proximal extremity 13 of the hypo tube 12 and also by a suitable means such as an adhesive (not shown). The sleeve 78 is provided with feed through holes 79 which are in registration with feed through holes 81 provided in the plastic sleeve 77. As shown particularly in FIG. 1, the shape-memory element 31, the conductor 41 and the pull elements 66 are bonded respectively to the slip rings 71, 72, 73 and 74 to form an electrical connection therewith.

An extension sleeve 86 formed of a suitable material such as stainless steel having the same outside diameter as the flexible elongate tubular member 12 is mounted on the other end of the sleeve 78 by a suitable means such as a slip fit and by an adhesive (not shown). The sleeve 86 has a length so it extends proximally 1–2 centimeters and is provided with a coarse helical thread 87 extending into the inner bore 88 of the sleeve 86. The cylindrical extension 86 makes it possible for the proximal extremity 13 of the flexible elongate tubular member 12 to receive a docking or exchange wire 91 which can be provided with a cooperating mating thread 92 so that it can be inserted and removed from the sleeve extension 86. It should be appreciated that other means other than threads 87 and 92 can be utilized for making a connection between the sleeve extension 86 and the docking wire 91 of a type well known to those skilled in the art.

Means is provided for supplying electrical energy and for controlling the flexible elongate device 11 and consists of a handle assembly 101 (see FIG. 7) which is provided with a connector 102 connected by a cable 103 to a control console 104 connected to a power cord 105 for connecting to a suitable source of power such as 110 volts AC.

The handle assembly 101 consists of a cylindrical member 106 formed of a suitable insulated material such as plastic and has a bore 107. A mounting block 108 is mounted within the bore 107 by suitable means such as an adhesive (not shown) and is provided with a bore 109 which is adapted to receive the proximal extremity 13 of the flexible elongate member 12. The mounting block 108 is provided with a plurality of contact elements 111 which are adapted to engage the slip rings 71, 72, 73 carried by the proximal extremity 13 of the flexible elongate device 11. The contact elements 111 are connected to a plurality of conductors 112 which are connected into the connector 102 and to the cable 103 to the control console 104.

Means is provided as a part of the handle assembly 101 for causing rotation of the flexible elongate device 111 and consists of a knurled knob 116 which is rotatably mounted on the cylindrical member 106 and which is secured to the proximal extremity 13 of the flexible elongate member 12 by suitable means such as an adhesive (not shown) so that when the knob 116 is rotated the flexible elongate device 11 is rotated. A matching member 117 matching the knob 116 is provided on the other end of the cylindrical member 106 and is secured thereto by a suitable means such as threads (not shown) and carries the connector 102. The control console 104 includes a variable current power supply of a conventional type which is provided with two outputs one of which is controlled by a knob 121 to control the location of the bend and the other of which is controlled by another knob 122 for controlling the reach and/or stiffness of the flexible elongate device 11.

An alternative embodiment of the present invention showing the control console 104 and the handle assembly 101 incorporated into a single unit in the form of a handle assembly 126 is shown in FIG. 8. The handle assembly 126 consists of a cylindrical member 127 which is provided with a mounting block 128 in a compartment 129. The mounting block 128 is provided with a bore 131 which is adapted to receive the proximal extremity 13 of the flexible elongate member 12 and carries contact members 132 which are adapted to engage the slip rings 71, 72, 73 and 74 to make electrical contact therewith. The contact members 132 are connected by conductors (not shown) to an electronics module 136 carried within a compartment 137 in the cylindrical member 127. The module 136 is adapted to receive power from a battery 141 mounted in a compartment 142. A rheostat 146 is mounted within a compartment 147 and is provided with a control knob 148 and is connected by wiring (not shown) to the electronics module 136. The knob 148 is provided for controlling the reach or stiffness and corresponds to the knob 122 provided on the control console 104. A slide type potentiometer is mounted in the compartment 137 above the electronics module 136 and is provided with a slide control 152 which is adapted to be moved longitudinally of the cylindrical member 27 in a slot 153 and corresponds to the bend control knob 121 provided on the console 104. A knurled knob 156 is mounted on the proximal extremity 13 of the flexible elongate member 12 and is secured thereto by a suitable means such as an adhesive (not shown) and is disposed immediately distal of the cylindrical member 127 and can be used for rotation of the flexible elongate device 11 as hereinbefore described in conjunction with the knob 116.

Operation and use of the flexible elongate device 11 with the controls shown in FIGS. 7 and 8 may now be briefly described as follows. One of the controls is for controlling the location of the bend in the distal extremity of the flexible elongate device 11 and the other control is for controlling the reach and/or stiffness of the distal extremity of the flexible elongate device 11. Operation of the control 121 and the slider 152 to increase the amount of current flow into the pull wire 66 causes the pull wire 66 to shrink as a result of $I^2R$ heating causing it to pull on the pull element 51 to cause the tip to deflect in a single plane with the bend for the tip deflection taking place at the weakest point along the distal extremity of the shape-memory element 51. The location of this bend point and/or the stiffness of the shape-memory element 31 can be adjusted by the control knob 122 on console 104 on the handle assembly 126. As the current flow increases through the shape-memory element 31 increases beyond a certain amount, the plated portion 31b begins to heat up because of $I^2R$ heating and is transformed from a martensitic state to an austenitic state to become austenitic and thus stiffer so that the bend point moves distally to a less stiff section or portion 31c. As a thickness of the plating 37 increases, the amount of current flowing through successive sections of the portion 31c will decrease proportional to the thickness of the tapered plating 37. Further increase of the current flow will cause $I^2R$ heating of progressive sections of the portion 31c because more current will pass through the shape-memory element 31 to cause it to become progressively austenitic and therefore stiffer causing the bend location to be progressively shifted distally as the current flow is increased. When a maximum current flow is reached, the entire shape-memory element becomes austenitic and thus becomes stiff permitting very little deflection and providing a stiffness which makes it possible for the guide wire to cross stenoses in a vessel.

If it is desired to shift a bend location proximally rather than distally, it is merely necessary to decrease the current flow through the shape memory element 31 by an appropriate adjustment of the control knobs 122 or 148.

The bending can be controlled by operation of the knob 121 on the control console 104 or the knob 152 on the handle assembly 126 to cause energy to be supplied to the pull wire 66 to cause it to be heated by $I^2R$ heating to shorten the same to cause pulling on the pull element 51. This causes the distal extremity 14 of the flexible elongate element 12 to be bent in a single plane so that a vessel can be negotiated by the guide wire under the control of the physician operating the device 11. The amount of bending can be readily adjusted by controlling the movement of the control knob 121 or the control knob 152. When it is desired to achieve a particular type of bend, this can be accomplished by the control knob 122 and 148 to adjust the location of the bend. The same controls can be utilized to adjust the stiffness so that the tip of the flexible elongate device 11 can be caused to cross a stenoses which may be partly calcified.

From the foregoing construction it can be seen that a flexible elongate device has been provided which is particularly useful for guide wires but which also may be utilized in catheters in which the distal extremity can be bent in a single plane with the bend location being adjustable longitudinally of the axis of the device so that different types of bends can be placed in the distal extremity of the device facilitating navigating tortuous small blood vessels of the heart. When a stenosis is encountered in the vessel, the stiffness of the distal extremity can be adjusted so that the flexible elongate device can be made to cross the stenosis.

In the construction shown, it is possible to provide a shape-memory element which requires a minimum of solder connections. By way of example, by providing plating on the proximal extremity of the shape-memory element it is possible to eliminate the need for a separate conductor for carrying electrical energy to the distal extremity of the shape-memory element so that the current can flow through the plating and not through the shape-memory thereby reducing the $I^2R$ heating taking place in the shape-memory element where it is not desired. The Nitinol material which is utilized for steering the distal extremity of the flexible elongate device is offset from the portions of the shape-memory element 31 in which bends are to be formed. Thus, any $I^2R$ heating of the pull wire will not effect the shape-memory element operation because the pull wire is staggered or offset with respect to the shape-memory element 31. Therefore any heating which occurs because of the operation of the pull wire will not effect the operation of the shape-memory element 31. The construction hereinbefore disclosed is also particularly advantageous in that it makes it possible to make small diameter guide wires, as for example from 0.008 inches to 0.014 inches, while still making it possible to achieve variable stiffness, variable bend location with single plane tip deflection and with a tip which is radiopaque.

What is claimed is:

1. A flexible elongate device comprising a flexible elongate member having proximal and distal extremities, a shape-memory element disposed in the flexible elongate member and being capable of assuming martensitic and austenitic states and having first and second portions, a layer of conductive material formed on at least one of said portions, said layer having a conductivity greater than that of the shape-memory element and means connected to the proximal extremity for supplying electrical current to the shape-memory element, said conductive layer serving to conduct current and shunting current flow around that portion of the shape-memory element having the layer of conductive material thereon.

2. A device as in claim 1 wherein said layer has a substantially uniform thickness.

3. A device as in claim 1 wherein said layer has a thickness which is tapered.

4. A device as in claim 3 wherein said thickness increases in a direction towards the distal extremity of the flexible elongate member.

5. A device as in claim 1 wherein at least one of said first and second portions is free of a layer of conductive material.

6. A device as in claim 1 wherein said shape-memory element has a third portion, the first, second and third portions being identified in a direction from the distal extremity of the shape-memory element towards the proximal extremity, said first portion having a conductive layer formed thereon which is tapered in thickness with the thickness increasing in a direction towards the distal extremity of the flexible elongate member, said second portion being free of a layer of conducting material and said third portion having a layer of conductive material thereon of substantially uniform thickness.

7. A device as claim 1 together with a pull element secured to the distal extremity of the flexible elongate member and means secured to the flexible elongate member for applying a pulling force to the pulling member so that the distal extremity of the flexible elongate member can be bent in a single plane.

8. A device as in claim 7 wherein said means for supplying a pulling force to the pull member consists of a member having a negative coefficient of expansion so that it contracts upon being heated and means for supplying electrical current to the member having a negative coefficient of expansion.

9. A device as in claim 8 wherein said member having a negative coefficient of expansion is disposed in the flexible elongate member so that it is offset with respect to the first and second portions so that any heat generated by the member having a negative coefficient of expansion will not affect the first and second portions of the shape-memory element.

10. A device as in claim 1 wherein at least a portion of the distal extremity of the flexible elongate member is formed of a radiopaque material.

11. A flexible elongate device with an adjustable stiffness comprising a flexible elongate member having proximal and distal extremities, means including a pully member secured to the distal extremity and slidably mounted in the flexible elongate member and for applying a pulling force to the distal extremity to cause bending of the distal extremity of the flexible elongate member, a shape-memory element disposed in the distal extremity of the flexible elongate member and means coupled to the proximal extremity of the flexible elongate member for supplying heat to the shape-memory element to adjust the stiffness of the shape-memory element and to thereby affect the bending of the distal extremity of the flexible elongate member.

12. A device as in claim 11 together with means mounted on the shape-memory element for determining where bending will occur in the distal extremity of flexible elongate member when the pull member is actuated.

13. A device as in claim 12 together with means for shifting the location of the bend in the distal extremity while an actuating force is applied to the pull member.

14. A flexible elongate device comprising a flexible elongate member having proximal and distal extremities, means secured to the distal extremity for applying a pulling force to the distal extremity to cause bending of the distal extremity of the flexible elongate member, a shape-memory element disposed in the distal extremity of the flexible elongate member and means secured to the proximal extremity of the flexible elongate member for supplying electrical current to the shape-memory element to vary the stiffness of the shape-memory element, with means carried by the shape-memory element for determining where bending will occur in the distal extremity of flexible elongate member when the pull member is actuated and means for shifting the location of the bend in the distal extremity while force is applied to the pull member, said means for shifting the location of the bend including a layer of conducting material formed on the shape-memory element, said layer of conducting having a thickness which is tapered in a direction extending longitudinally of the shape-memory element.

15. A device as in claim 14 wherein said layer increases in thickness in a direction towards the distal extremity of the flexible elongate member.

16. A device as in claim 14 wherein said means for applying a pulling force to the distal extremity of the flexible elongate member includes a member within the flexible elongate member but which is spaced away in a direction proximal of the distal extremity of the flexible elongate member so that heat generated by $I^2R$ heating will not influence the shape-memory element having the layer of tapered thickness thereon.

17. In a method for controlling the distal extremity of a flexible elongate member with an adjustable stiffness and having proximal and distal extremities, applying a pulling force to the distal extremity to cause the distal extremity to bend in a single plane and adjusting the location of the bend in the distal extremity while the pulling force is being applied to obtain different types of bends in the distal extremity of the flexible elongate member.

18. A method as in claim 17 together with the step of progressively adjusting the location of the bend so that different types of bends can be provided.

19. In a method for controlling the distal extremity of a flexible elongate member having proximal and distal extremities by the use of a shape-memory element disposed within the distal extremity of the flexible elongate member, applying a pulling force from the proximal extremity to the distal extremity of the flexible elongate member to cause bending of the same in a single plane, supplying an electrical current to the shape-memory element to increase the stiffness of at least a portion of the shape-memory element and shunting the current flow around at least a portion of the shape-memory element.

20. In a method for controlling the distal extremity of a flexible elongate member having proximal and distal extremities by the use of a shape-memory element disposed within the distal extremity of the flexible elongate member, applying a pulling force from the proximal extremity to the distal extremity of the flexible elongate member to cause bending of the same in a single plane, supplying an electrical current to the shape-memory element to increase the stiffness of at least a portion of the shape-memory element and shunting current flow around that at least a portion of the shape-memory element in a progressive manner.

21. In a method for controlling the distal extremity of a flexible elongate member having proximal and distal extremities by the use of a shape-memory element disposed within the distal extremity of the flexible elongate member, applying a pulling force from the proximal extremity to the distal extremity of the flexible elongate member to cause bending of the same in a single plane, supplying an electrical current to the shape-memory element to increase the stiffness of at least a portion of the shape-memory element and shunting the current flow around at least a portion of the shape-memory element and shunting the current flow around the proximal extremity of the shape-memory element.

* * * * *